US005638830A

United States Patent [19]
Valade

[11] Patent Number: 5,638,830
[45] Date of Patent: Jun. 17, 1997

[54] PROCESS AND DEVICE FOR AUTOMATIC VERIFICATION OF THE POSITIONING OF A SURGICAL INSTRUMENT

[75] Inventor: Jean-François Valade, Bordeaux, France

[73] Assignee: Satelec S.A., Merignac, France

[21] Appl. No.: 341,582

[22] PCT Filed: May 26, 1993

[86] PCT No.: PCT/FR93/00514

§ 371 Date: Nov. 22, 1994

§ 102(e) Date: Nov. 22, 1994

[87] PCT Pub. No.: WO93/24071

PCT Pub. Date: Dec. 9, 1993

[30] Foreign Application Priority Data

May 26, 1992 [FR] France ................................. 92 06441

[51] Int. Cl.$^6$ ........................................... A61B 19/00
[52] U.S. Cl. ................................. 128/897; 128/734
[58] Field of Search ..................... 128/897–99, 734; 433/27–28, 72, 75, 86, 98

[56] References Cited

U.S. PATENT DOCUMENTS

| 4,243,388 | 1/1981 | Arai . |
| 4,595,019 | 6/1986 | Shene et al. . |
| 5,026,387 | 6/1991 | Thomas . |

Primary Examiner—Angela D. Sykes
Assistant Examiner—John P. Lacyk
Attorney, Agent, or Firm—Young & Thompson

[57] ABSTRACT

Process and device for use in surgery comprising a conducting element capable of shifting from a first medium to a second medium, which can measure an electrical parameter such as conductance and which can present a variation threshold during its movement when the conducting element is in contact with the second medium. The device can determine the variation of the electrical parameter during the movement of the conducting element in the first medium, as well as detect at least one predefined critical value and produce a signal when this critical value is detected.

10 Claims, 1 Drawing Sheet

PROCESS AND DEVICE FOR AUTOMATIC VERIFICATION OF THE POSITIONING OF A SURGICAL INSTRUMENT

BACKGROUND OF THE INVENTION

The present invention relates to a device intended for providing automatic verification of the positioning of a surgical instrument with respect to elements of the body of a patient, and in particular to a device adapted to ensure verification of the positioning of an odontological tool in a radicular canal with respect to the apex of a tooth. The present invention also relates to a process for detecting the apex of a tooth.

It is known that, in surgery, the positioning of an instrument must sometimes be made at a determined place of a given medium, close to a second medium, in an area not visible of the surgeon.

This is the case in odontology where the preparation of the canal must respond to two essential objectives, namely, to extirpate the pulpy tissue and evacuate it from the radicular canal and, secondly, to machine the latter to give it an appropriate shape, adapted to receive a hermetic stop perfectly obturating the canal hermetically up to its terminal part.

For reasons of rapidity and efficiency, this machining is usually affected with the aid of an apparatus comprising a tool, such as a file, which is subjected to vibrations whose frequency lies within the ultrasonic domain.

One problem encountered by the practitioner carrying out such a technique is that of ensuring a clean and quasi-perfect "machining" of the radicular canal of the patient's tooth, while avoiding going beyond the apex thereof, i.e. the constriction located at the bottom of said canal and which separates this latter from the patient's mucous membrane, for fear of causing the patient serious injury.

The means available to the practitioner to ensure such detection are, first conventional localization methods such as tactile sensitivity or radio-graphic monitoring and, second electronic monitoring means.

These latter usually measure the electrical resistance existing between a first electrode, or gingival electrode, placed in contact with the patient's gum, and a second electrode, sometimes constituted by the file itself, which is introduced in the radicular canal, a decrease in resistance at the level of the apical constriction indicating the proximity of the mucuous membrane and therefore of the apex of the tooth.

French Patent 85/17632 discloses an apparatus for monitoring, during the progress of a probe or a tool at rest, inside the radicular canal, the variation of a physical parameter such as conductance, which undergoes a sudden increase when the probe arrives in the immediate proximity of the apex. Once the proximity of the apex is determined; the practitioner then engages on his tool a marking stop generally by an elastic washer which is maintained thereon by friction and which, during the "machining" phase, will enable the to know at what moment his tool will reach the apex.

Although such a device makes it possible to define with high precision the relative position of the tool with respect to the apex, it requires the positioning of a marking stop on the tool. The positioning of the marking stop, precisely by reason of its mode of fixation, is neither precise nor reliable. As an example, the marking stop may shift beyond its initial setting, which during the machining phase, may cause the apex of the tooth to be exceeded.

As an alternative, the intervention is then made in two phases, namely a first phase of measurement and a second phase of actual machining, which involves a loss of time both for the surgeon and for his patient.

Finally, in this type of device, the may be a sudden increase in the conductivity measured by reason of diverse causes, without the tool being in the vicinity of the apex of the tooth, so that there is a risk of stopping the "machining" of the radicular canal before it has arrived at the apex thereof. Of course, to avoid this drawback, the value of the threshold of detection of the apex may be increased but, in that case, there is a risk, during the phase of machining of the radicular canal, of continuing the latter beyond the apex, and into the patient's mucous membrane.

SUMMARY OF THE INVENTION

It is an object of the present invention to overcome these drawbacks by proposing a process and a device of the type mentioned above while avoiding the use of a marking stop which may possibly be used in one sole step, and which is insensitive to a sudden and isolated variation of the electrical parameter measured.

The present invention thus has for its object a device for use in surgery comprising a conducting element adapted to move in a first medium, towards a second medium, comprising means for measuring an electrical parameter, such as conductance for example, capable of presenting a variation threshold during said displacement when the conducting element is in contact with the second medium, characterized in that it comprises means for determining the drift, or slope, of the electrical parameter, all along the displacement of the conducting element in the first medium, means for detecting at least one predetermined critical value of the drift or slope, and means for producing a signal when this determined value attains same critical value.

In one embodiment of the invention, the conducting element consists of a tool which vibrates under the action of an ultrasound generator. The tool comprises servo-control means controlling its operational parameters, namely its amplitude and/or its vibration frequency. When the value of the drift or slope of the electric parameter attains a critical value, the servo-control modifies the operational parameters of the tool in accordance with a predetermined function, which may lead to complete stoppage of the vibration of the tool.

The present invention also has for its object a process for detecting the apex of a tooth. A element conducting electric current is introduced in the radicular canal and is displaced therein towards the apex of the tooth. During this displacement, an electrical parameter capable of presenting a variation threshold when the conducting element lies at the apex of the tooth is measured. This involves the steps of determining the drift, or slope, of said electric parameter all along the displacement of the conducting element, and producing a signal when the value of this drift, or slope, attains a predetermined critical value.

In one embodiment of the invention, the tool is animated by a movement of vibration during its displacement in the radicular canal, so as to machine the walls thereof. When the drift, or slope, of said electric parameter attain its critical value, the operational parameters of the tool are modified, namely its amplitude and/or its vibration frequency, in accordance with a predetermined function.

BRIEF DESCRIPTION OF THE DRAWINGS

An embodiment of the present invention will be described hereinafter by way of non-limiting example, with reference to the accompanying drawings, in which.

DESCRIPTION OF THE PREFERRED EMBODIMENTS

Figure 1:
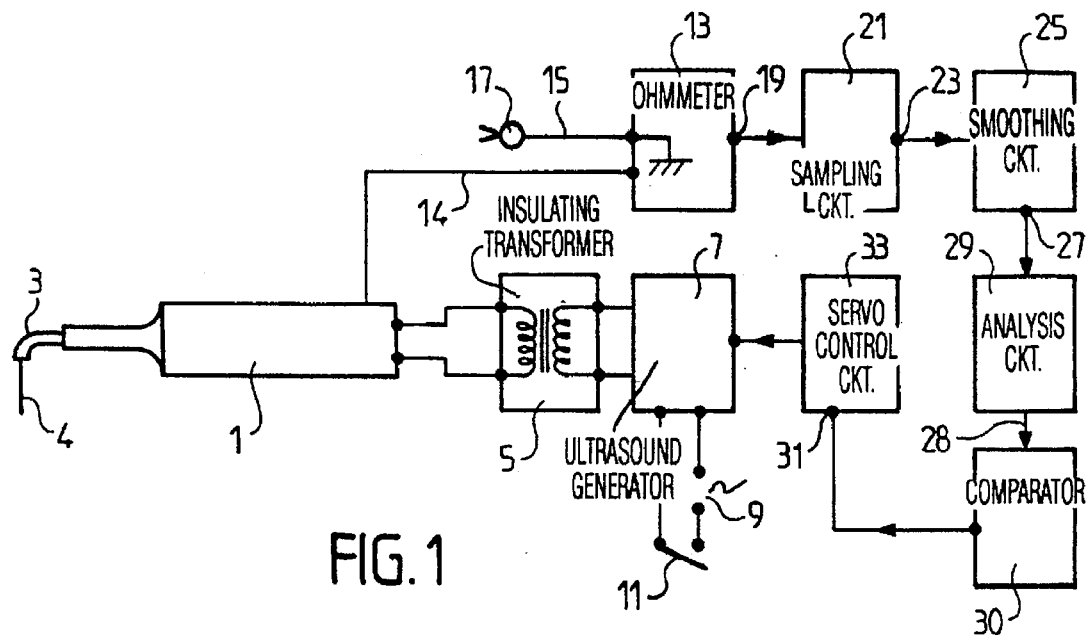
FIG. 1 is a block diagram of the device according to the invention.

The device according to the invention, described with reference to FIG. 1, is intended to ensure the preparation of a tooth, i.e. the cleaning and machining of its radicular canal.

It comprises an ultrasonic transducer 1 on the front part of which is fixed, in removable and interchangeable manner, a sonotrode 3 provided with a surgical instrument, namely, in the present case, a file 4. The transducer 1 is connected, via an insulating transformer 5, to an ultrasound generator 7 which is itself connected to electric supply means 9 through a switch 11 actuated by a control pedal.

The device also comprises means for measuring the conductance existing between the end of the file 4 and the patient's mucous membrane. These means are constituted by an ohmmeter 13, of which one terminal is connected to the file 4 by a conducting wire 14 and the other terminal is connected to the patient's mucous membrane by a conducting wire 15 whose end is provided with a buccal clip 17. The output terminal 19 of the ohmmeter 13 is connected to a sampling circuit 21, whose output 23 is itself connected to a smoothing circuit 25. The output 27 of the smoothing circuit 25 is connected to an analysis circuit 29 whose output 28 is connected to a comparator 30, ensuring a comparison of the output signal of the analysis circuit 29 with a threshold value corresponding to a predetermined critical value. The output 31 of the comparator 30 is in turn connected to a servo-control circuit 33 ensuring control of the ultrasound generator 7.

Under these conditions, the device according to the invention functions as follows:

After having switched on the ultrasound generator 7, by closing the switch 11 by means of the control pedal, the practitioner displaces the file 4 inside the radicular canal of the tooth, and measures, all along this displacement, by means of the ohmmeter 13, the resistance existing between the end of the file 4 and the patient's mucous membrane. The signal obtained at the output 19 of the ohmmeter 13 is furnished to the sampling circuit 21 which, in a first step, reverses the signal furnished by the ohmmeter 13 to convert it into a conductance signal, then effects sampling of this analog signal with a determined sampling frequency appropriate for the precision of the measurement which it is desired to effect. The sampled signals obtained at the output of the sampling circuit 21 are then smoothed by the smoothing circuit 25, for example, by a process of digital processing, so that, at the output 27 of the smoothing circuit 25, the curve obtained, or characteristic X, (cf. FIG. 2) represents an average of the measurements made and gives the variation of the conductance $C=1/R$ as a function of the depth of penetration x of the file 4 in the radicular canal. Such treatment attenuates, and even totally eliminates in certain cases, the different parasitic peaks which, according to the prior art, were capable of disturbing the characteristic X and of indicating the proximity of the apex. The smoothed signal is then furnished to the analysis circuit 29 which determines, at each instant all along the progress of the tool 4 in the radicular canal, the instantaneous variation of the conductance C, i.e. the slope $p$ at all points of the characteristic X.

Figure 2:
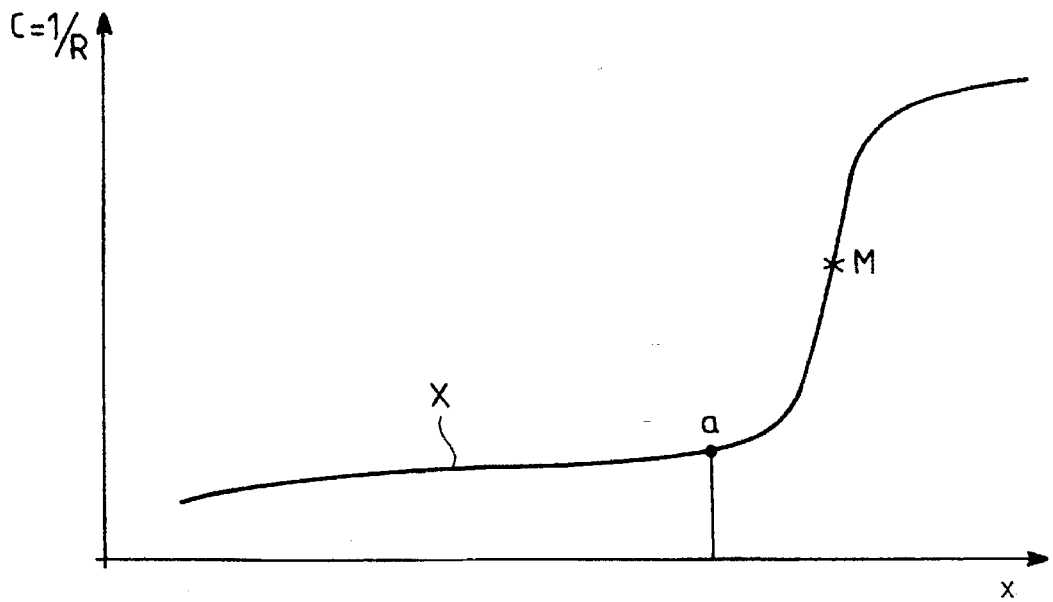
FIG. 2 is a diagram showing the characteristic curve of the variation of the electric conductance during the progress of conducting element in the radicular canal of a patient's tooth.

As shown in FIG. 2, when, during displacement of the file 4 inside the radicular canal, one lies at a point $\underline{a}$ of the characteristic X, where the slope $p_a$ of the characteristic, determined by the analysis circuit 29, is equal to the critical value $P_c$, necessitating a parameter change, the comparator circuit 30 emits a signal to the servo-control circuit 33. The servo control circuit 33 then regulates the ultrasound generator 7 in order to modify, for example, the amplitude of the vibrations to which the file 4 is subjected, in accordance with a predetermined function, which may result in the complete stoppage of the file 4.

Figure 3:
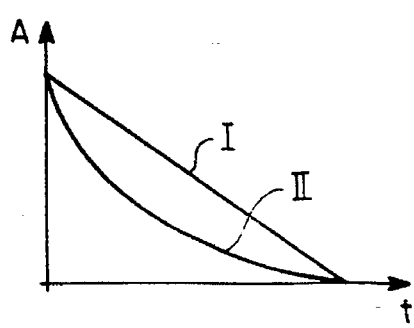
FIG. 3 is a diagram showing two curves of the operational parameters of the tool as a function of time.

This predetermined law of variation may for example be linear as a function of time t (curve I of FIG. 3), i.e. the amplitude A of the vibrations of the file 4 decreases proportionally in time, leading to a total stoppage of the vibrations. Of course, such a law of variation in time may be other than linear (curve II of FIG. 3). It may also be such that it controls an immediate stoppage of the vibrations of the file 4.

Further the device according to the invention may be provided with selection means making it possible to choose, from a series of preprogrammed functions of the amplitude of the vibrations as a function of time, the one which is the most appropriate for the work to be effected.

For example, the invention thus makes it possible, as one approaches the apex, to reduce the amplitude of the vibrations and consequently the risks associated with passing beyond said apex.

Of course, said these functions may be applied not only to the variation of amplitude of the tool but also to the frequency of its vibrations.

It will also be noted that the precision of the device may be improved by increasing the sampling frequency as one approaches the apex, i.e., when the slope of the characteristic X attains a certain fraction of the maximum slope $p_M$ thereof.

In another embodiment of the invention, the predetermined critical value $p_c$ of the slope may be determined automatically. To that end, prior to the machining step, a step of preliminary measurement is performed, for which, either a specific probe or the file 4 itself, may be used. During this step, without activating the ultrasound generator 7 so as not to vibrate the file, the file 4, acting as a probe, is introduced inside the radicular canal and is displaced therein measurements are taken until the maximum slope $p_M$ which is located in FIG. 2 at point $\underline{M}$ is detected. As a function of this maximum slope $p_M$, the slope or critical value $p_c$ is determined either by a shift towards the origin representing the desired safety margin or by giving the critical value $p_c$ a value equal to a fraction of the maximum slope $p_M$. In this way, a critical value $P_c$ equal to half the maximum slope $p_M$ of the characteristic X makes it possible, in the majority of cases, to obtain an efficient detection of the apex. This value may be associated with the choice of the function of the operational parameters of the tool, by software and/or by electronic means. The value $p_c$ may then be stored in a memory and the second step of the process may then be undertaken, namely the machining of the radicular canal, such that as soon as the slope of the characteristic X attains the critical value $p_c$, the device according to the invention will carry out the process of variation of the operational parameters of the tool, i.e. the amplitude and/or frequency of vibration thereof.

While the invention has been described with relation to various preferred embodiments, various modifications and adaptations thereof will be readily apparent to those skilled in the art. All such modifications and adaptation that fall within the scope of the appended claims are intended to be covered thereby.

I claim:

1. Device for use in surgery comprising a conducting element adapted to be displaced in a first medium, towards a second medium, further comprising means for measuring an electrical parameter; said device presenting a variation threshold, during said displacement, when said conducting element is in contact with said second medium, said device further comprising means for detecting at least one predetermined critical value of said electrical parameter and means for producing a signal when said determined value attains said critical value, wherein said device further comprises:

means for determining the drift, or slope, of said electrical parameter, along displacement of said conducting element in said first medium.

2. Device according to claim 1, wherein said device comprises means for storing the value of the maximum drift, or slope, of said electrical parameter, during said displacement of said conducting element, and further comprising analysis means for determining the critical value of said electrical parameter from said value of the maximum drift or slope.

3. Device according to claim 2, wherein said critical value is substantially equal to half the value of said maximum drift, or slope.

4. Device according to claim 1, wherein said conducting element comprises a tool, said device comprising an ultrasound generator which vibrates said tool, said device further comprising servo-control means controlling the operational parameters of said tool, said parameters being one or more of amplitude and vibration frequency, said servo-control means being adapted, when the value of said drift or slope of said electrical parameter attains said critical value, to modify said operational parameters of said tool as a predetermined function of time.

5. Process for detecting the apex of a tooth comprising the steps:

introducing an element conducting electric current in the radicular canal of said tooth, said conducting element being displaced in said radicular canal towards said apex of said tooth, measuring an electric parameter which presents a variation threshold when said conducting element lies at the apex of said tooth during said displacement, determining the drift, or slope, of said electric parameter along said displacement of said conducting element, and producing a signal when the value of said drift, or slope, attains a predetermined critical value.

6. Process according to claim 5, wherein samples of said measured values of said electric parameter are taken, said samples being used to produce a smoothed curve representing the variations of said electrical parameter as a function of the displacement of said conducting element.

7. Process according to claim 6, wherein the frequency of said samples is increased when said drift, or slope, of said smoothed curve attains a value close to said critical value.

8. Process according to claim 5, wherein said critical value is determined from the measurement of the maximum drift, or slope of said smoothed curve.

9. Process according to claim 5, wherein said element is a vibrating tool, said tool machining the walls of said radicular canal, the operational parameters of the vibration of said tool being modified as a predetermined function of time when said drift, or slope, of said electrical parameter attains said critical value.

10. Process according to claim 9, wherein said modification of said operational parameters results in complete stoppage of the vibration of said tool.

* * * * *